United States Patent
Peterson et al.

(12)

(10) Patent No.: US 6,207,696 B1
(45) Date of Patent: Mar. 27, 2001

(54) COMPOSITIONS AND METHODS FOR THE PROPHYLAXIS AND TREATMENT OF DYSMENORRHEA, ENDOMETRIOSIS, AND PRE-TERM LABOR, USING HISTIDINE

(75) Inventors: John Peterson, Dickinson, TX (US); Peter G. Thomas, Charlottesville, VA (US)

(73) Assignee: Cytos Pharamaceuticals, LLC, Durham, NC (US)

( * ) Notice: Subject to any disclaimer, the term of this patent is extended or adjusted under 35 U.S.C. 154(b) by 0 days.

(21) Appl. No.: 09/153,354

(22) Filed: Sep. 15, 1998

(51) Int. Cl.$^7$ .................................................. A61K 31/415
(52) U.S. Cl. ........................ 514/400; 514/899; 514/967
(58) Field of Search ................................. 514/400, 899, 514/967

(56) References Cited

PUBLICATIONS

CA 90:3565, Cox et al.*
CA 108:198416, Euro–Celtique S. A.*

* cited by examiner

*Primary Examiner*—Kimberly Jordan
(74) *Attorney, Agent, or Firm*—Susan Petraglia; Isaac Angres

(57) ABSTRACT

The present invention relates to methods and compositions for preventing or treating conditions or disorders of the female reproductive system by administering an effective dosage of histidine alone or in combination with other therapeutic agents. The invention relates also to novel physical compositions and delivery devices for administering histidine effectively to a female subject in need of either prophylaxis or treatment of certain disorders of the reproductive system.

61 Claims, 8 Drawing Sheets

FIG. 5

TABLE 1: $^1$H NMR Assignments for PGE$_2$ – Imidazole Complex

| Atom # | δ (ppm) (chemical shift) | Integral/multiplicity *key |
|---|---|---|
| IMD H2 | 8.81 | 1H/s |
| IMD H4 | 7.46 | 1H/s |
| IMD H5 | 7.62 | 1H/s |
| H2 | 2.29 | 2H/t |
| H3 | 1.57 | 2H/m |
| H4 | 1.99 | 2H/br q |
| H5 | 5.45 | 1H/br q |
| H6 | 5.32 | 1H/br q |
| H7 | 2.36 | 2H/br t |
| H8 | 2.58 | 1H/m |
| H10 | 3.07 | 1H/dd |
| H10 | 2.79 | 1H/br dd |
| H11 | 4.84 | 1H/br q |
| H12 | 2.9 | 1H/br q |
| H13 | 5.55 | 1H/dd |
| H14 | 5.37 | 1H/dd |
| H15 | 4.03 | 1H/br q |
| H16 | 1.39 | 1H/m |
| H16 | 1.29 | 1H/m |
| H17 | 1.16 1.08 | 2H/m |
| H18 | 1.08 | 2H/m |
| H19 | 1.16 | 2H/m |
| CH3-20 | 0.76 | 3H/br t |

*Key:
s= singlet
br= broad
dd= doublet of doublets
t= triplet
q= quartet
m= multiplet

COMPOSITIONS AND METHODS FOR THE PROPHYLAXIS AND TREATMENT OF DYSMENORRHEA, ENDOMETRIOSIS, AND PRE-TERM LABOR, USING HISTIDINE

FIELD OF THE INVENTION

The present invention relates to methods and compositions for preventing or treating conditions or disorders of the reproductive system of a female mammal, by administering an effective dosage of histidine alone or in combination with other therapeutic agents. The invention relates also to novel physical compositions, e.g., delivery devices, for administering histidine effectively to the reproductive system of a female subject in need of either prophylaxis or treatment.

BACKGROUND OF THE INVENTION

Dysmenorrhea is a common repetitive disorder affecting female adolescents and women, and is closely associated with the menstrual cycle. Over the years, there has been a widespread mischaracterization of dysmenorrhea as simply, a painful menstruation or menstrual cramping. There are several types of dysmenorrhea, as defined for example in Taber's Cyclopedic Medical Dictionary ($12^{th}$ edition), however the two types that are most prevalent and most prevalently studied are primary dysmenorrhea and secondary dysmenorrhea. In primary dysmenorrhea there is no underlying or associated organic pathology of either the uterus, fallopian tubes, or ovaries. Where an organic pathology of the type just mentioned does exist, the resulting dysmenorrhea is termed secondary. Some causes of secondary dysmenorrhea are endometriosis, uterine myomas (and polyps and adhesions), ovarian cysts, adenomyosis, pelvic inflammatory disease (PID), and the presence of an intrauterine device. For a thorough modern day treatment of the etiologic bases of dysmennorrhea and premenstrual syndrome, including studies and a historical perspective of therapy regimens, see, for example, Dawood M. D., M. Y. et al, "*Premenstrual Syndrome and Dysmenorrhea*", (Urban & Schwarzenberg 1985) incorporated herein in pertinent part by reference.

While primary and secondary dysmenorrheas require different management or therapy (the latter type usually requiring surgery), both types involve increased levels of prostaglandin synthesis. The increased prostaglandin synthesis results from the loss of hormonal support at menses (i.e., low progesterone), which triggers the release of arachidonic acid from phospholipids under the action of phospholipase $A_2$. Arachidonic acid is the essential starting material for prostaglandin biosynthesis, in the presence of the enzyme cyclooxygenase. Prostaglandins are smooth muscle-stimulating agents, hence giving rise to increased uterine contractility. The major prostaglandins involved in uterine function are $PGE_2$, $PGF_{2\alpha}$, and $PGI_2$(prostacyclin). The key role of prostaglandins in dysmenorrhea was first noted in 1957 by Pickles, who observed their presence in menstrual fluid. Pickles later identified the principle component of the prostaglandins as a mixture of $PGF_{2\alpha}$ and $PGE_2$. Another researcher by the name of von Euler pin-pointed $PGF_{2\alpha}$ (also known as "prostaglandin $F_{2\alpha}$") as the agent responsible for stimulating the normal expulsive contractions of the myometrium. Hence, the symptomology of dysmenorrhea resembles that of the side effects of prostaglandin adminin-stration. Namely, nausea, vomiting, diarrhea, vasoconstriction (i.e., uterine ischemia), and severe uterine cramps. Irritability and other psychological disturbances are also symptoms of dysmenorrhea. The physical pain of dysmenorrheic uterine cramping or hypercontractility is directly the result of increased production of prostaglandin $F_{2\alpha}$ either before or with onset of menstruation.

The modalities for managing or treating primary dysmenorrhea are different from those for managing or treating secondary dysmenorrhea. This is due in large part to the fact that the latter almost always ultimately requires a surgical intervention (oftentimes preceded by an unsuccessful attempt at drug therapy), whereas the former can be effectively brought under control by administering drug therapy.

The chief therapies for primary dysmenorrhea are administration of oral contraceptives (endocrine therapy) and prostaglandin synthetase inhibitors. Essentially all non-steroidal antiinflammatory agents (NSAIDS) fall into the latter group. Oral contraceptives are the ideal choice for treating a dysmenorrheic woman where that woman's primary objective is birth control. Birth control pills are believed reduce prostaglandin levels in menstrual fluid by 1) reducing the volume of menstrual fluid by suppression of endometrial tissue growth, and 2) by inhibiting ovulation, thereby creating an endocrine milieu wherein prostaglandins are low and luteal phase progesterone levels, believed to be necessary for prostaglandin biosynthesis, are absent. However, oral contraceptives are not the primary choice of birth control for all women of child-bearing years for a number of reasons. For example, birth control pills carry numerous contraindications, and they must be taken regularly at least three (sometimes four) weeks of the month.

Prostaglandin synthetase inhibitors (PSIs), on the other hand, are given typically 2–3 days of the menstrual cycle for treating primary dysmenorrhea. There are two types of PSIs. Type I prostaglandin synthetase inhibitors are those that inhibit the enzyme cyclo-oxygenase, thereby blocking the conversion of arachidonic acid to cyclic endoperoxides. Type II prostaglandin synthetase inhibitors are those that inhibit the isomerase and reductase enzymes, thereby preventing the conversion of endoperoxide to prostaglandin. NSAIDS that are type I PSIs include aspirin, indomethacin, meclofenamic acid, and ibuprofen. NSAIDS that are type II PSIs include phenylbutazone and p-chloromercuribenzoate. A large number of compounds fall under the umbrella of NSAIDS and all demonstrate, in varying degrees, the ability to inhibit prostaglandin synethesis. These include aryl carboxylic and arylalkanoic acids, acetic acid analogs, propionic acid analogs, fenamates, and enolic acids (including pyrazolidinediones). While NSAIDS are predominantly the treatment of choice for primary dysmenorrhea over oral contraceptives, NSAIDS are not without side effects. The predominant side effects are various gastrointestinal disorders (e.g., gastric ulceration), renal dysfunction, and disturbances of the central nervous system (e.g., headache, dizziness, and drowsiness).

Other drug-related therapies for dysmenorrhea include progesterone-medicated intrauterine devices, and calcium antagonists (to inhibit muscle contraction). Limited efficacy has been observed with administration of betamimetic agents, and tocolytic agents (i.e., ethanol).

The management of secondary dysmenorrhea generally entails elucidating the underlying organic pathology and correcting it usually with surgery. Any medicinal therapy administered to a woman with secondary dysmenorrhea is an interim measure to bring some relief of symptoms while the underlying pathology is elucidated and/or the patient awaits appropriate surgery. However, there are certain instances of secondary dysmenorrhea where a medicinal management is appropriate. For example, women who develop dysmenorrhea from the use of an IUD should be prescribed an effective prostaglandin synthetase inhibitor. Also, hormone therapies, e.g., with danazol and certain gonadotropin releasing hormone analogues, have been effective in relieving the dysmenorrhea and pelvic pain caused by endometriosis. Combination therapy of danazol in conjunction with oral contraceptives has been shown not only to relieve the pain associated with endometriosis, but also to cause a regression of the disorder.

Admittedly, great strides have been made in the past forty years in the understanding of the nature and types of dysmenorrhea, as well as in how to manage or treat this disorder that affects most, if not all, of adolescent females and women. While the benefits offered by the highly efficacious prostaglandin synthetase inhibitors (NSAIDS) seem to outweigh their side effects, and the same could possibly be said for oral contraceptive therapy, there is still a need in the art for the discovery of other therapeutic agents of equal or greater efficacy to NSAIDS and having far fewer contraindications for the management of dysmenorrhea, endometriosis, and pre-term labor.

Carnouvis, C. P. et al, *Am. J. Physiol.*, 255, F685–9 (1988) and Burch, R. M. et al, *J. Pharmacol. Exp. Ther.*, 210, 344–8 (1979) have demonstrated in in vitro studies with toad urinary bladder preparations that histidine decreased $PGE_2$ synthesis therein. Steinhauer, H. B. et al, *Clin. Nephrol.*, 24, 63–68 (1985) report that histidine diminishes $PGE_2$ and thromboxane $B_2$ levels in spontaneous murine autoimmune disease. Also, Steinhauer, H. B. et al, *Prostaglandins Leukotrienes Med.*, 13, 211–16 (1984).

U.S. Pat. No. 5,417,224 (Petrus et al) discloses tampons impregnated with numerous types of active agents, including, generally, amino acids for treating cervical tears and cervicitis. However, as yet unrecognized or suggested in the art, the present invention is based on the discovery that the amino acid histidine is both effective and highly safe in treating a number of reproductive disorders in the human female, and also in certain other female mammals.

SUMMARY OF THE INVENTION

The present invention is based on the discovery that histidine, when administered in effective quantities, is useful as a prophylactic or therapeutic agent for preventing or treating prostaglandin-related disorders of the female reproductive system. For example, one object of the invention is a method for treating or preventing the onset of primary dysmenorrhea.

Another object of the invention is a method for treating certain types of secondary dysmenorrhea by administering an effective quantity of histidine. Within this context, the invention relates further to methods for the treatment of endometriosis by administering an effective quantity of histidine. Also within the context of treating secondary dysmenorrhea, the invention also embodies, for example, methods for treating secondary dysmenorrhea arising in a human female as the result of intrauterine device use, treating polycystic ovary syndrome, or a number of other disorders of the female reproductive system.

Yet still another object of invention is a method for treating or preventing the onset of pre-term labor in a pregnant female, by administering an amount of histidine effective to prevent the onset of pre-term labor or to control it sufficiently to extend pregnancy to as close to full term as possible.

The invention also embodies novel compositions and delivery devices containing effective amounts of histidine for administration in any of the above-described methodologies. Methodologies and compositions for co-administering histidine in combination with one or more additional therapeutic agents useful in treating any of the prostaglandin disorders also form a part of the invention.

These and other objects will be further understood and appreciated from the following detailed description of the invention, the examples, and the appended claims.

BRIEF DESCRIPTION OF THE FIGURES

FIG. 5 is a table of proton NMR assignments for $PGE_2$-imidazole complex.

DETAILED DESCRIPTION OF THE INVENTION

Figure 1:
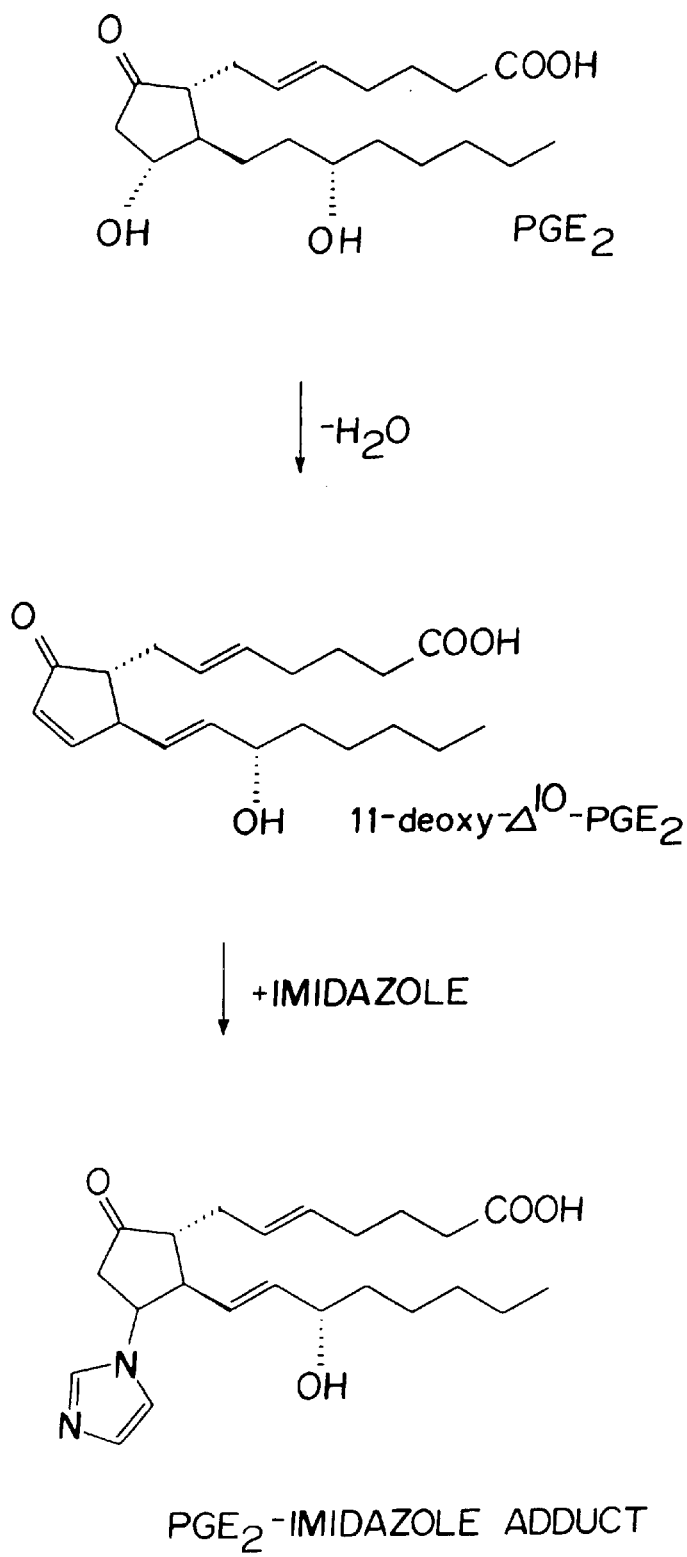
FIG. 1 depicts the reaction scheme between prostaglandin $PGE_2$ and the imidazole moiety of histidine.

The present invention provides effective and highly safe methodologies for to prophylaxis or treatment of prostaglandin-mediated disorders of the female reproductive system, by using histidine as the therapeutically active agent. More particularly, prostaglandins are at work, for example, in primary dysmenorrhea (frequently given the short-hand abbreviation "menstrual cramping"), secondary dysmenorrhea, in the pain associated with endometriosis, in pre-term or premature labor, and in other instances of uterine hypercontractility and ischemia. However, the invention is not to be construed as limited to treating prostaglandin-mediated disorders in human females only, but also to treating other female mammals when the disorder is capable of diagnosis (e.g., pre-term labor). Also, in those embodiments where the subject being treated is a human female, the term "human female" means both women within their child-bearing years and post- menopausal women using hormone replacement therapy. In certain embodiments, the woman treated is an insulin-resistant woman.

The methodologies herein described are for either prophylaxis or treatment of certain female reproductive disorders in which prostaglandins are involved. By "prophylaxis" is meant the ability to prevent the onset of the chemical chain of events, e.g., by inhibiting prostaglandin synthesis or inactivating prostaglandin molecules before expression of the cascade of sequelae. By "treatment" is meant the ability to effectively abate the chemical chain of events once they have begun or to alleviate one or more sequelae or symptoms.

One of the present embodiments is a method for preventing the onset of dysmenorrhea or treating the sequelae thereof in a human female by administering to her female at a time prior to menses and/or at commencement of menses an amount of histidine that is effective to prevent onset of dysmenorrhea or to treat the sequelae thereof. As will be described in greater detail below, the effective amount of histidine is administered in conjunction with at least one pharmacologically acceptable carrier. The chief manifestations, or sequelae, of dysmenorrhea are nausea, vomiting, diarrhea, vasoconstriction, i.e., uterine ischemia, and (which leads to) severe uterine cramping. Irritability and other psychological disturbances are also sequelae of dysmenorrhea and can be abated or prevented by histidine administration. Both primary and secondary dysmenorrheas are intended for treatment or prophylaxis. Cramps associated with pre-menstruation and/or menses are a symptom of primary dysmenorrhea and can be prevented or treated by preferably commencing histidine administration to the woman either prior to onset of menstruation or, alternatively, on first occurrence of menstrual cramps, with continued administration for as many days of menses that the menstrual cramps persist.

The secondary dysmenorrheas that are subject to treatment within the present context have an underlying pathologic origin, such as endometriosis, pelvic inflammation, pelvic infection, adenomyosis, uterine myoma, uterine polyps, uterine adhesions, congenital malformations of the Mullerian system, cervical stenosis, ovarian cysts, pelvic congestion syndrome, polycystic ovary syndrome(PCOS), and Allen-Master's syndrome. In certain of these underlying pathologies the secondary dysmenorrhea is a sequela thereof, and in others the dysmenorrhea results from treating the underlying condition, e.g., as in PCOS (which is a major cause of infertility, especially in insulin-resistant women). Treatment of secondary dysmennorrhea that arises in a woman from the presence of a contraceptive intrauterine device(IUD) or any other IUD is also a part of the present embodiment.

For this embodiment and all others to now be described, the therapeutically active agent histidine encompasses either enantiomer, a racemic mixture, non-racemic mixtures, the free base form of histidine, and pharmacologically acceptable salts that can be reduced to L- or D-histidine. These histidine compounds are readily commerically available from numerous chemical and pharmaceutical suppliers. Where it is useful in the practice of the invention to employ a mixture of D- and L- histidine that is enriched in one enantiomer, such a mixture can be prepared by physically admixing the desired quantity of each of the enantiomers. Histidine derivatives, analogs, or pro-drug derivatives of histidine which are readily understood by a chemist of skill in the art are also intended for use in the present embodiments. More preferably, the histidine compound is L-histidine or a pharmaceutically acceptable salt of L-histidine.

The administration of histidine according to another embodiment of the invention is useful in treating pelvic pain in women suffering from endometriosis. The typical "cure" for endometriosis is surgical oophorectomy, the most effective way to eliminate ovarian sex steroid production, the cause of endometriosis. Thus histidine administration in this context is a therapy for secondary dysmenorrhea as a consequence of endometriosis. However, it is also contemplated that histidine when coadministered with certain hormonal agents (e.g., Meldrum, R. J. et al, *Obstet. & Gynecol.*, V. 62, no. 4, 480–5 (1983); and Meldrum, R. J. et al , *J. Clin. Endocrinol. & Metab.*, V. 54, no. 5, 1081–83 (1982) not only is useful in treating the secondary aspects of the underlying pathology, but also is effective in causing a regression of the pathology itself. Coadministration regimens include, for example, histidine in conjunction with danazol (widely used to treat endometriosis) and histidine in conjuction with GnRH-a, a long-acting gonadotropin-releasing hormone analogue. Thus, this embodiment provides a "medical" oophorectomy, as an alternative to surgical castration.

However, surgical intervention will be the primary treatment for endometriosis and for many other underlying organic pathologies causing a secondary dysmennorrhea. Prostaglandins are formed rapidly in damaged tissue. The tissue at and around the excision locus will be damaged or traumatized surgically, thereby raising the levels of prostaglandins and prostaglandin side effects in that area. Therefore, among the present embodiments is a method for inactivating prostaglandins formed during oophorectomy or other surgical procedure to correct an underlying pathology of a secondary dysmenorrhea, by administering an effective amount of histidine to the patient before, during, and after the surgical procedure.

Another embodiment of the invention is the prevention of onset of, or therapy for controlling a pre-term labor in a pregnant woman or other pregnant mammal. These objectives are accomplished by administering to pregnant woman or mammal an amount of D-histidine, L-histidine, a therapeutically acceptable salt of histidine which can be reduced to D- or L-histidine, or mixtures thereof, that is effective to prevent, or control the pre-term labor by extending it to substantially a full-term. Histidine can be administered efficaciously via oral formulations, intravenous formulations, intravaginal devices such as a medicated tampon, by vaginal transmucosal formualtions, or using any combination of these. It is anticipated that the use of larger more efficacious amounts of histidine will either obviate the need for use of other pre-term labor therapeutics, e.g., Sulindac(clinoril), that carry the risk of side effects on mother and unborn child. At the very least it is contemplated herein that histidine coadministered with other pre-term labor therapeutics will permit the coadministration of the latter in reduced, less-potentially harmful amounts.

As stated previously in the Background of the Invention, certain therapeutic agents for prostaglandin-mediated conditions act at the level of inhibiting prostaglandin synthesis (i.e., prostaglandin synthetase inhibitors). While not wishing to be bound by any one particular theory for the underlying mode of action, the therapeutic activity observed from histidine administration is believed to be due to inactivation of prostaglandins formed rather than inhibition of prostaglandin synthesis. More specifically, unpublished studies of one of the present coinventors reveal that L-histidine chemically reacts with $PGE_2$ thereby disabling or inactivating the prostaglandin in its role in the inflammatory cascade (e.g., $PGE_2$'s stimulatory effect on adenylate cyclase). The chemical transformation of $PGE_2$ with imidazole is shown in FIG. 1 and is thought to proceed by an initial dehydration of the prostaglandin molecule to yield the alpha, beta-unsaturated ketone 11-deoxy-$\Delta^{10}$-$PGE_2$. The dehydration is thought to be acid/base catalyzed by imidazole, or by the imidazolyl ring of L-histidine or histidine analogs. For example, addition of imidazole by Michael-addition to the alpha,beta-unsaturated ketone yields the 11-deoxy-11-imidazolyl-$PGE_2$. The NMR spectrum (FIG. 2) and mass spectra (FIGS. 3A and 3B) confirm that the product of the reaction mechanism shown in FIG. 1, $PGE_2$-imidazole, is formed. A similar covalent bond is formed between $PGE_2$ and L-histidine.

Mass Spectrometry analysis of the $PGE_2$-imidazole complex. FAB-MS analyses of the $PGE_2$-imidazole complex isolated from either HPLC peak (FIG. 3—peak 1 or peak 2) showed an intense $(M+H)^+$pseudomolecular ion at m/z 403. Similar data were obtained with ESI-MS. The presence of a single imidazole moiety in the complex was confirmed by analysis of a U-$[^{15}N]$-imidazole product, which gave an intense pseudomolecular ion at m/z 405. The presence of a free carboxylic acid was indicated by successful esterification of the $PGE_2$-imidazole complex. This was demonstrated by the FAB-MS spectrum of the product which showed a $(M+H)^+$ pseudomolecular ion at m/z 419 (methanol) and m/z 422 ($d_3$-methanol). Analysis of the acetylated complex (U-[$^{15}$N]-labeled) by ESI-MS showed an (M+H)$^+$ at m/z 489 consistent with the reaction of two acetyl groups.

Figure 2A:
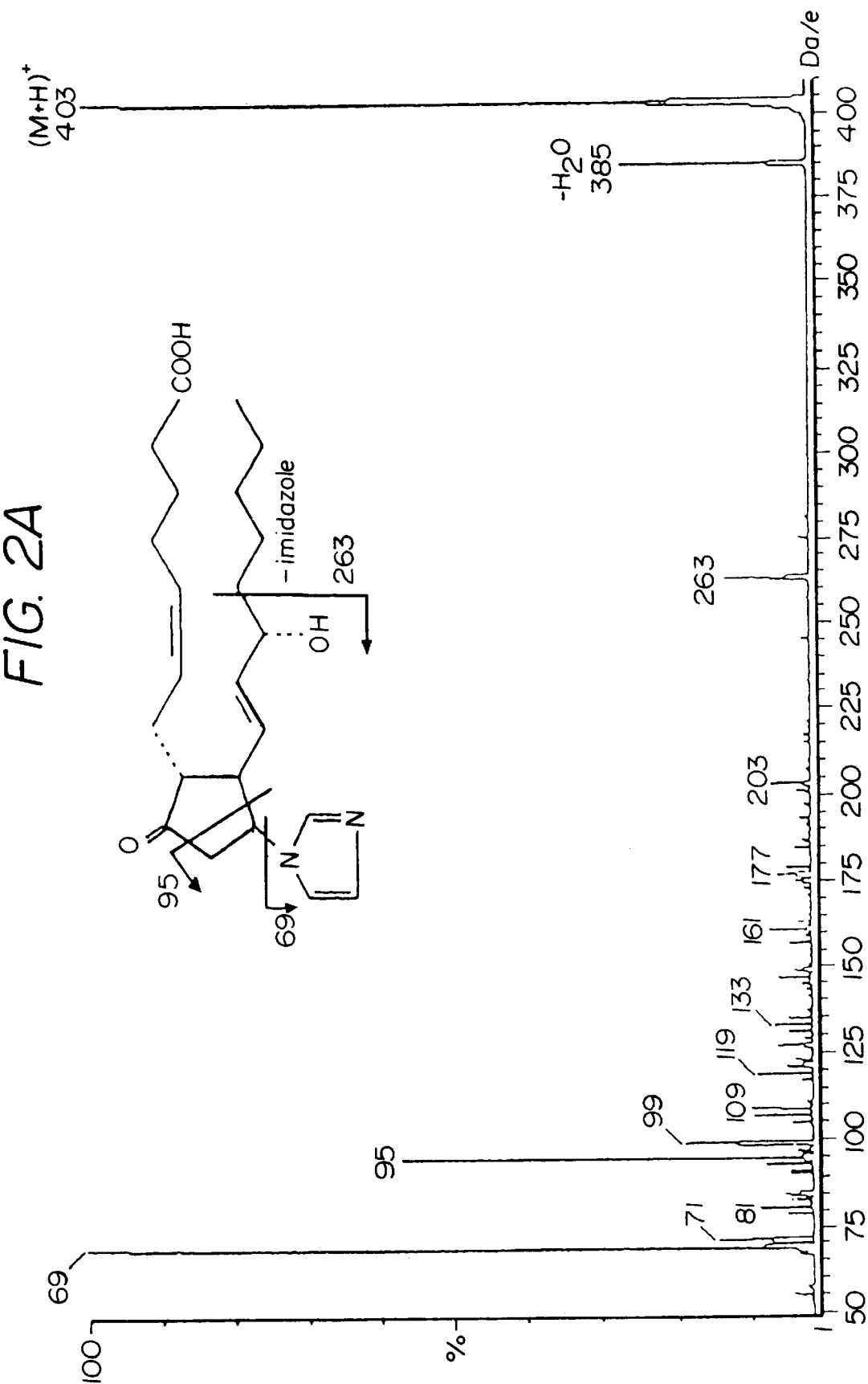
FIGS. 2A and 2B are mass spectral analyses for $PGE_2$-imidazole.
Figure 2B:
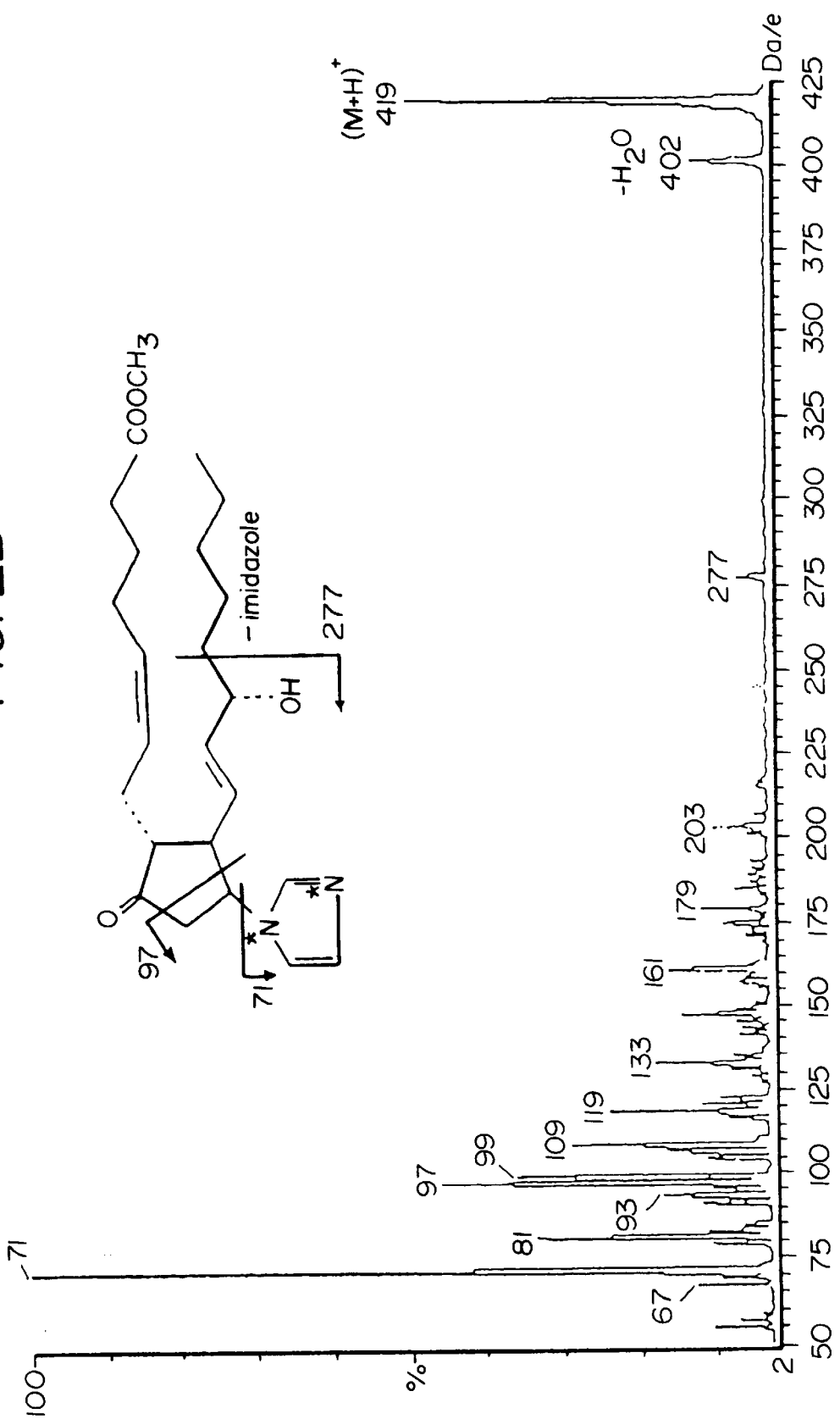
Figure 3:
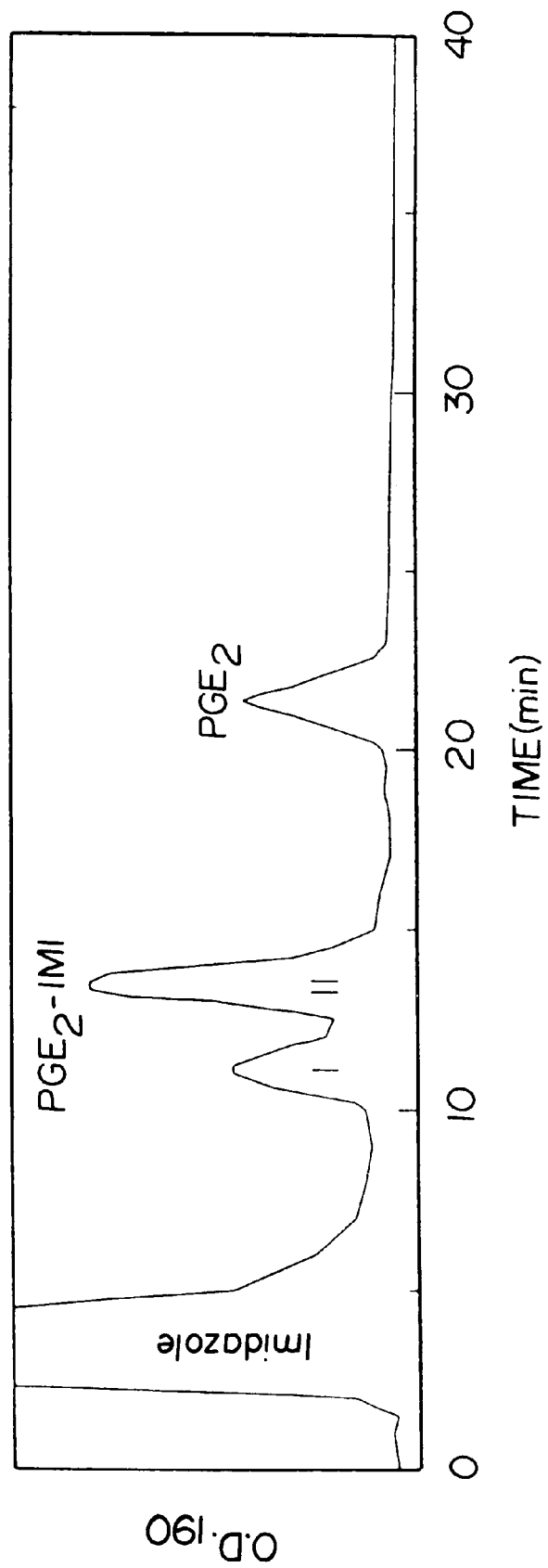
FIG. 3 is a C-18 reverse-phase chromatogram of $PGE_2$-imidazole complex obtained at 190 nm.

Collisionally-induced dissociation (CID) of the PGE$_2$-imidazole complex and a number of derivatives was also performed (following methods outlined in Zirrolli, J. A. et al, *J. Am. Soc. Mass Spectrom*, 1, 325–335 (1990)). The spectrum obtained for the PGE$_2$-imidazole complex is illustrated in FIG. 2A. The major daughter ions at m/z 69 and 95 can be assigned to fragmentation of the imidazole moiety and this was confirmed by the corresponding daughter ion spectra of the U-[$^{15}$N]-labeled complex, which showed similar intense daughter ions at m/z 71 and 97. The signal at In/z 263, which was retained in the spectrum of the U-[$^{15}$N]-complex, was consistent with a concerted fragmentation mechanism involving elimination of the imidazole and cleavage at C15. Elimination of water from the molecular ion accounted for the signal m/z 385, whereas the low intensity ions between m/z 100–200 were consistent with cleavage along the methylene chains. FIG. 2B illustrates the ESI-MS/MS daughter ion spectrum for the esterified PGE$_2$-imidazole complex and lends support to the ion assignments already given.

Derivation of the structure of the PGE$_2$-imidazole complex by NMR.

Figure 4A:
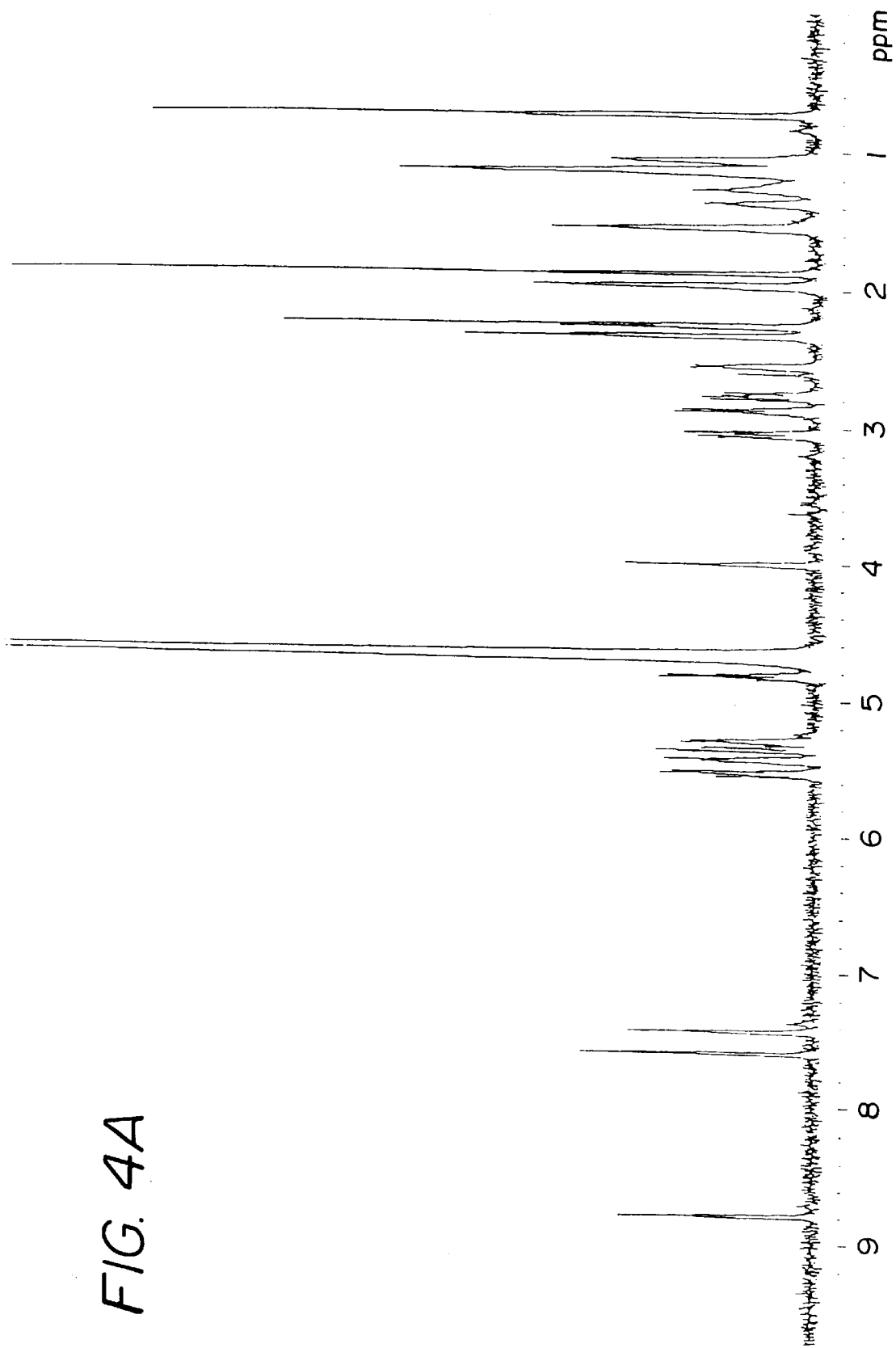
FIGS. 4A–C are the NMR spectra of the reaction product of $PGE_2$ and imidazole.
Figure 4B:
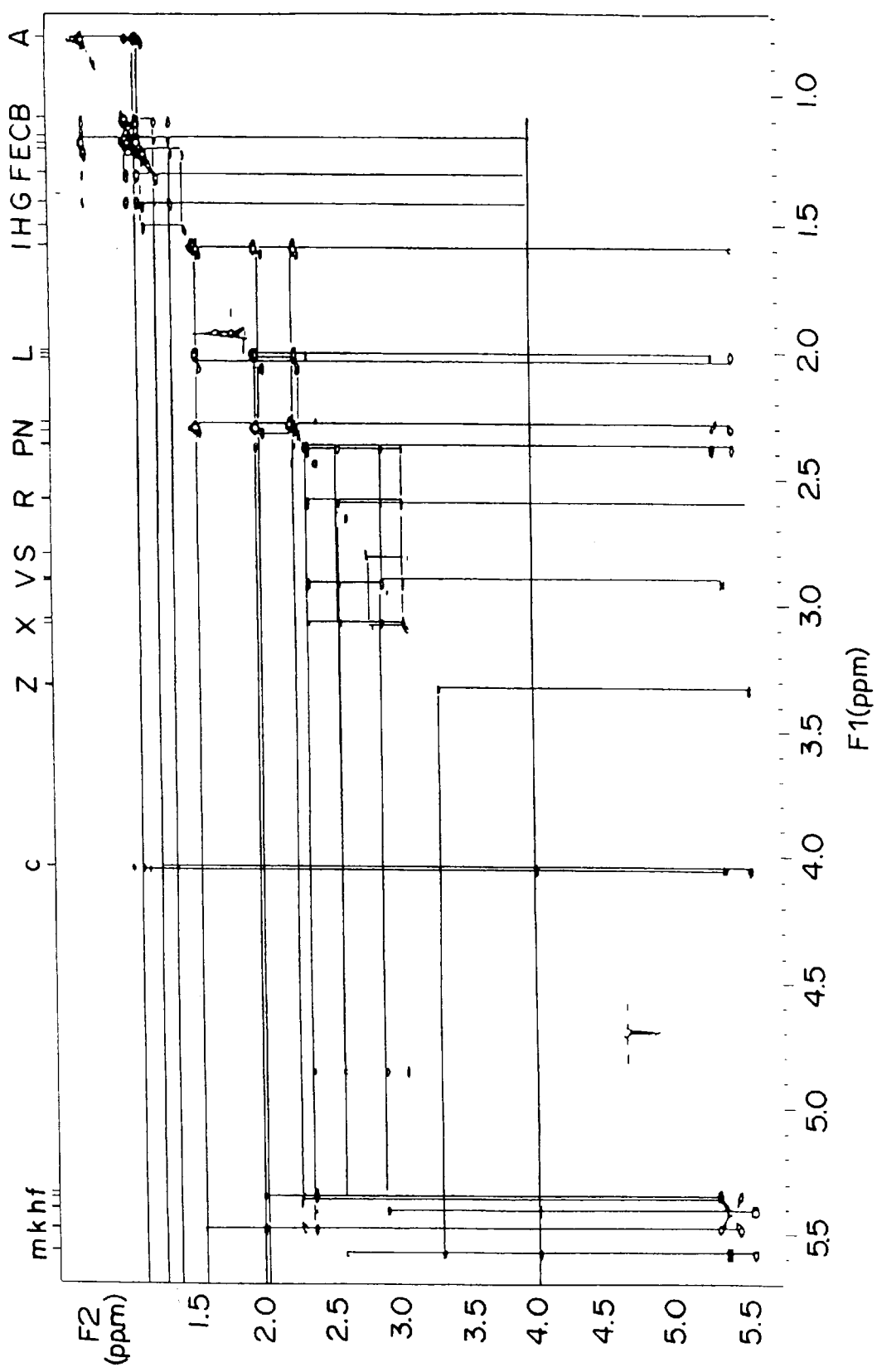
Figure 4C:
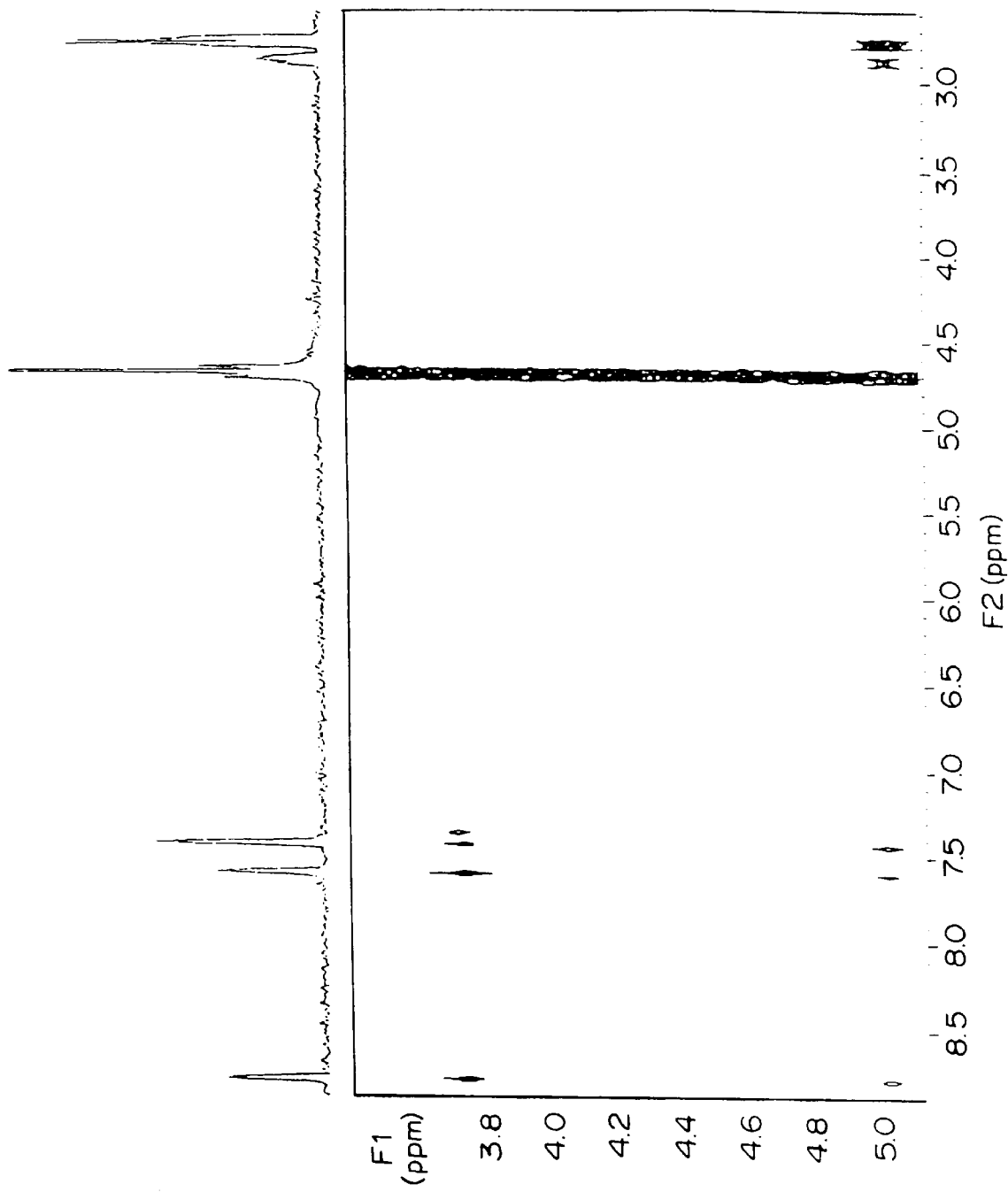

Specific information about the chemical structure of PGE$_2$-imidazole was derived from NMR analysis and fragmentation patterns by mass spectrometry. The 1D $^1$H NMR spectrum of the PGE$_2$-imidazole complex is shown in FIG. 4. The assignments of the $^1$H signals was accomplished through analysis of the 2D COSY and TOCSY spectra (FIG. 4B). During the course of the 2D NMR spectra acquisition, some degradation of the sample was noted with several new peaks appearing. The assignments were straightforward, with crosspeaks in the TOCSY spectra connecting many of the coupled protons. Thus, TOCSY correlation is seen for H-13 (5.55 ppm) to 14, H-15 and H-12 (in order of crosspeak appearance; see FIG. 1 and FIG. 5 for identification of protons). H-5 (5.45 ppm) shows correlation to H-7, H-2, H-4, and H-3. H-14 (5.37 ppm) is correlated to H-13, H-15, and H-12. H-6 (5.32 ppm) is correlated to H-5, H-7, H-2 and H-4. H-11 (4.84 ppm) shows correlation in the dimension F-2 to H-10, H-12, H-8 and H-7 (water presaturation obscures the diagnol peak and correlation in the F1 dimension). H-15 (4.03ppm) is correlated to H-13, H-14, H-15, H-16, H-16', H-17 and H-17'. H-10 (3.07 ppm) is correlated to H-11, H-12, H-8 and H-7. Continuing upfield, H-12, H-8, H-7, H-2, H-4 and H-3 show the expected crosspeaks. Finally H-19 (1.16 ppm), H-18 (1.08 ppm) and H-20 (0.76 ppm) show correlation to each other as well as H-15 and H-16, thus completing the sequential connectivity of the protons of the prostaglandin adduct. The downfield imidazole ring protons were assigned through the COSY and TOCSY spectra, as well as the $^{15}$N/$^1$H HMBC spectrum of the U-$^{15}$N-labeled imidazole PGE$_2$-imidazole complex sample (FIG. 4C). The latter spectrum correlated the $^{15}$N/$^1$H coupled imidazole nitrogens with the imidazole protons H-2, H-4 and H-5 as well as two of the prostaglandin protons. Thus, N-1 of the imidazole (5.02 ppm) shows correlation to imidazole H-2 (8.81 ppm), H-4 (7.46 ppm), and H5 (7.62 ppm) as well as protaglandin protons H-12 (2.90 ppm) and H-10$^1$(2.79 ppm). Unfortunately, either because of small coupling or partial signal saturation due to the proximate HDO resonance, only a small, tentatively identified cross peak to the H-11 proton was observed. The correlation to both H-10 and H-12 (large three-bond coupling) confirms the site of covalent attachment of the imidazole ring to the prostaglandin framework. In addition the only significant chemical shift perturbations in the complex relative to those of the free PGE$_2$ is found for H-11 (+0.74 ppm; + values represent downfield shift for the complex), H-10, 10 (+0.65 and +0.35 ppm), H-12 (+0.47 ppm), H-8 (0.27ppm) and H-14 (–0.19 ppm).

Because histidine is a naturally occurring amino acid, it is well-tolerated at high doses without attendant toxicities and side effects. In general, an effective prophylactic or therapeutic amount of histidine in the context of the invention is from about 500 mg to 30 g daily for human applications. Where the present embodiments are applicable to larger mammals, e.g., in veterinary applications for pre-term labor, the upper limit may be greater and readily determined by the treating veterinarian considering the age and weight of the patient and the severity of the condition.

Compositions and methods for the coadministration of therapeutic doses of histidine with other therapeutically active agents form a part of the present invention. In methods of coadministering histidine with one or more additional therapeutically active agents, it is envisioned that all of the active agents can be administered either simultaneously or sequentially. Accordingly, the effective dose of histidine may be co-formulated with the additional active agent(s) in a single composition. Alternatively, where sequential co-administration is more appropriate or practical, then separate dosage forms for administration by the same or different route of administration, will be used. Regardless of whether the coadministration occurs in one composition or two (or more), in certain cases it is possible to reduce the dosage of the additional therapeutic agent from what it would be if it were administered by itself (i.e., without histidine). This reduction is possible in view of the fact that histidine can be dosed at larger efficacious amounts without side effects. Therefore, an important benefit of coadministering another therapeutic with histidine is an anticipated reduction in the side effects attributable to the former. For example, this benefit is readily appreciated in drugs used for managing or preventing pre-term labor, where side effects can pose significant risk to the unborn child (such as, e.g., fetal respiratory distress). Even NSAIDs, which are generally regarded as safe, have side effects such as renal dysfunction and gastric ulceration if taken on a habitual or sustained basis. It is also contemplated that when combining a therapeutically effective amount of histidine with another therapeutically active agent, that a potentiated (i.e., more than additive) level of prophylaxis or therapy may be obtained.

In those instances where it is advantageous to co-administer histidine with one or more additional therapeutically active agents known and used in the art, the dose of the additional therapeutically active agent is typically a pharmacologically recommended effective dose. More preferably, in order to reduce the potential for harmful side effects, the dose of the additional therapeutically active agent is less than the pharmacologically recommended effective dose but is nonetheless an amount which is beneficial when co-administered with an effective amount of histidine. The prescribing physician or veterinarian can routinely determine the reduced amount of the additional therapeutic agent necessary for co-administration with histidine in view of the specific needs of the patient being treated.

Compounds suitable for "another therapeutically active agent" (also referred to as "a second compound") are those agents which are useful for abating or treating disorders such as dysmenorrhea and pre-term labor, agents for treating endometrial pain (e.g., NSAIDs, hormones), and agents for treating underlying reproductive disorders which as a result of correction or abatement cause dysmenorrhea. Examples of therapeutic agents for treating dysmenorrhea include, but are not limited to, tocolytic oxytocin antagonists (e.g., $\beta_2$-adrenergic agonists (ritodrine, terbutalin, and albuterol), magnesium sulfate, ethanol, amide substituted spiroindanyl-camphorsulfonyl oxytocin antagonists, peptide oxytocin antagonists (e.g., as disclosed in U.S. Pat. No. 5,026,703) and spiro cyclic compounds such as spiro indene-piperidine disclosed e.g., in U.S. Pat. No. 5,670,509); nonsteroidal antiinflammatory drugs/prostaglandin synthetase inhibitors (e.g., aspirin, diflunisal, ibuprofen, indomethacin, clinoril, tolectin, zomepirac, naproxen, ketoprofen, suprofen, meclofenamate, meclofenamic acid, flufenamic acid, mefenamic acid, ketorolac, cataflam, diclofenac sodium, phenylbutazone, p-chloromercuribenzoate and piroxicam); calcium supplements, pharmaceutically acceptable salts of calcium, and other pharmaceutically-recognized administrable forms of calcium; a heteropolycyclo-substituted heterocyclic amide thromboxane $A_2$ receptor antagonist (e.g., ifetroban or a pharmaceutically acceptable salt thereof); certain amidinoureas (e.g., those disclosed in U.S. Pat. No. 4,241,087), antiiflammatory arylmethylene and arylmethyl-indenoimidazoles (e.g., disclosed in U.S. Pat. No. 4,548, 943); and therapeutic peptides (e.g., U.S. Pat. No. 4,728, 640). Representative therapeutic agents for treating endometriosis include hormones, especially contraceptive regimens, danazol, and long-acting gonadotropin-releasing hormone analogues; therapeutic peptides (e.g., those disclosed in U.S. Pat. No. 4,728,640 and U.S. Pat. No. 4,743, 589); and nonsteroidal antiinflammatory drugs, such as those recited previously. Representative therapeutic agents for managing pre-term or premature labor include certain NSAIDs (e.g., clinoril (Sulindac)), an activin antagonist (e.g., human follistatin, a polyclonal or monoclonal antibody or immunogenic fragment thereof capable of binding to activin, e.g., as described in U.S. Pat. No. 5,545,616); smooth muscle relaxant S-nitrosothiols; certain aromatase inhibitors (e.g., 4-hydroxy-4-androstene-3,17-dione or 4-acetoxy-4-androstene-3,17-dione); inhibitors of leukotriene biosynthesis, e.g.,aryl, hetero, polysubstituted indoles (e.g., as disclosed in U.S. Pat. No. 5,081,138 and U.S. Pat. No. 5,225,421); quinolin-2-ylmethoxy indoles, fluoro-substituted quinoline indoles, quinolin-2-ylmethoxy tetrahydrocarbazoles, tetrahydrocarbazole alkanoic acids, quinoline ether alkanoic acids, cycloalkyl(e.g., heptyl) indole alkanoic acids, indenyl hydroxamic acids, and hydroxy ureas. Many of these pre-term labor therapeutics (e.g., the tocolytic oxytocin receptor antagonists, the heteropolycyclo indoles, the quinolyl indoles, the tetrahydrocarbazole alkanoic acids and the cycloalkyl indole alkanoic acids to name a few) are also useful for treating dysmenorrhea. Representative therapeutic agents for treating ovary dysfunction include hormone therapeutics and D-chiroinositol. The above listings are intended to be representative, and not limiting, of the types of additional therapeutic agents that can advantageously be co-administered with a therapeutic amount of histidine. Other agents for treating female reproductive conditions or disorders and which are readily appreciated by the treating physician or veterinarian are also intended in the present embodiment.

Histidine in accordance with the invention is formulated in conjunction with at least a pharmaceutically acceptable carrier. There are numerous and diverse types of acceptable carriers which are readily appreciated by those skilled in the art depending on the route of histidine administration. The routes of histidine administration that are appropriate in the practice of the invention include oral, rectal, intraintestinal, intramuscular, intraperitoneal, intranasal, intravenous (I.V.), implant and transdermal. Optimized efficacy of the methodologies herein can be achieved in certain instances by combining two different routes of administration in a course of therapy. For example, intravaginal administration (e.g., medicated tampon, medicated IUD, vaginal suppository) of histidine combined with oral liquid or tablet administration of either histidine and/or another therapeutically active agent, such as a prostaglandin synthetase inhibitor. Alternatively, transmucosal (e.g., vaginal cream, foam, or gel) or transdermal (e.g., a patch) administration of histidine supplemented with an intranasal or IV administration of histidine.

Formulations suitable for parenteral administration conveniently comprise sterile aqueous preparations of histidine which are preferably isotonic with the blood of the recipient. Suitable such carrier solutions include phosphate buffered saline, saline, water, lactated ringers or dextrose (5% in water). Such formulations may be conveniently prepared by admixing histidine with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives (when the formulations are presented in multi-dose containers), buffers to provide a suitable pH value for the formulation, and sodium chloride, or glycerin, to render a formulation isotonic with the blood.

For I.V. administration, histidine may be used in free or salt form (for example, salts of alkali and alkaline earth metals such as sodium and calcium, respectively, salts if mineral acids such as HCl and sulfuric acid, or salts of organic acids, such as acetic acid. Amine addition salts may also be used in the practice of the invention, for example a phosphate amine addition salt. Examples of typical carriers are sterilized water, saline, and phosphate buffered saline. Optional additives include isotonic agents, stabilizers, pH controlling agents, agents necessary for the proper infusion of solutions, and water soluble nutrients.

Transmucosal or transdermal administration can be accomplished using preparations in the form of ointments, emulsions, gels, lotions, solutions(e.g., douches), creams or patches (in the case of transdermal delivery). Suitable pharmaceutical carriers for transmucosal or transdermal administration include, for example, polyethylene glycol, propylene glycol, glycerin, isopropanol, ethanol, oleic acid, N-methylpyrrolidone, sesame oil, olive oil, wood alcohol ointments, vaseline, and paraffin, or mixtures thereof. For transmucosal delivery of, e.g., a histidine-containing gel, cream, or ointment formulation to the vaginal mucosa, bioadhesive polymer-based carrier compositions are particularly useful. Suitable bioadhesive polymers are, e.g., those that are described in U.S. Pat. No. 4,615,697, the disclosure of which is incorporated herein by reference. Particularly useful polymers are crosslinked polycarboxylic acid polymers having a sufficiently high degee of crosslinking to impart the desired level of bioadhesion to the target epithelial surface. Representative bioadhesive polymer formulations are described, for example, in U.S. Pat. No. 5,543,150 and U.S. Pat. No. 5,667,492. Other additives suitable for incorporation into a bioadhesive polymer formulation for histidine include one or more of a preservative, a humectant, a lubricating agent and or moisturizing agent, a stabilizer, a pigment, a pH modifier (e.g., a base) and purified water. Depending on the formulation additives and the resulting viscosity, such formulations may be administered vaginally as a douche, with a plunger, or as a suppository.

When histidine is to be incorporated in a transdermal patch, the therapeutic dose can be incorporated either directly in an adhesive layer that fixes a drug impermeable backing to the skin of the treated-subject, or it can be incorporated in a matrix layer and released therefrom in controlled fashion. Suitable adhesive layer carriers for histidine include, for example, polyisobutenes, polyisobutylenes, polyacrylates, polyurethanes, polysiloxanes, polystyrene copolymers, EVA-copolymer, and polyether amide block copolymers. Suitable drug-releasing matrices include, for example, natural or synthetic rubbers, polymeric materials, such as EVA copolymers, thickened mineral oil, and petroleum jelly. Optional constituents for the transdermal administration of histidine include drug permeable rate-controlling membranes and penetration enhancers which are well known to those skilled in the transdermal formulation art.

Histidine-containing vaginal suppositories afford constant release over an extended period of time and are particularly useful in treating or preventing symptoms of dysmenorrhea prior to menstrual flow, e.g., at or prior to ovulation or just prior to onset of menses. Although not as direct a mode of administration as a vaginal suppository, rectal suppositories may also be used to deliver histidine. Typical base carrriers for suppositories include, for example, natural, synthetic or partially synthetic fats, waxes and derivative thereof from animal, vegetable, or mineral origin. Specific examples inlcude olive oil, corn oil, castor oil, hydrogenated oils, petrolatum, solid paraffin, liquid paraffin, carnuba wax, bees wax, lanolin partially or totally synthetic esters of glycerol fatty acid, mono, di, or triglycerides of saturated or unsaturated fatty acids, and others well known in the art. Other additives suitable for incorporation into a suppository of the invention include preservatives, stabilizers, surfactants, pigments, pH modifiers and purified water.

Medicated devices suitable for vaginal or cervical implant include medicated tampons, and medicated intrauterine devices (IUDs). A tampon may be impregnated and/or coated with efficacious amount of slow-release histidine for a period of time consonant with safe and hygienic tampon usage (typically one tampon every 4 to 8 hours). Examples of tampons impregnated or coated with sustained-release therapeutic agents are found, e.g., in U.S. Pat. Nos. 3,995,636, 4,186,742, 4,340,055, 4,582,717, 5,201,326, and 5,417,224, and the disclosures of which are incorporated herein by reference. Histidine can be incorporated/impregnated into an over-wrap sheet of non-woven material which is permeable by body fluids and which is superimposed on a first sheet of absorbent material which forms the corpus of the tampon when the sheets are rolled or formed into the desired tampon shape, with the histidine-containing layer remaining on the outermost surface. Alternatively, the histidine can be deposited between the corpus absorbent sheet and the permeable over-wrap sheet during manufacturing. Alternatively, histidine can be incorporated into a tampon cover made from a hardened collagen or gelatin foam with a release retardant material such as triglycerides of higher fatty acids melting at body temperature, for application to an absorbent natural or synthetic tampon core. Histidine can be incorporated into an adhesive coating composition comprised, e.g., of approximately 50/50 mixture of citric acid and sodium bicarbonate, for application to a tampon core. Another mode of manufacturing a histidine-impregnated tampon incorporates the histidine into a suppository base formulation which is melted, syringe-impregnated into tampons, and allowed to cool. Alternatively, pre-formed tampons can be coated with the melted suppository formulation containing the active agent. In either case, the result is a tampon that releases histidine gradually as the suppository base melts in the presence of body temperature. Useful suppository auxiliaries are those recited hereinbefore as well as those described in U.S. Pat. No. 4,582,717.

Medicated IUDs include noncontraceptive as well as contraceptive WUDs, non-bio-erodible, partially bio-erodible, and completely bio-erodible IuDs. Examples of active agent-releasing intrauterine devices that could be used in the practice of the present invention are described in U.S. Pat. Nos. 3,934,580, 3,993,057, and 4,016,270, incorporated herein by reference. Typically, the IUD is made of a flexible polymeric non-eroding core and is over-coated with a bio-erodible coat material containing histidine. Alternatively, the IUD core can be a bio-erodible material containing the histidine for sustained-release, and may or may not further comprise an active agent-releasing outer coat. The latter construction makes it unnecessary to remove the device after all of the medicament is released. For example, an active intrauterine device within the practice of the invention can consist of a non-bioerodible hydrophobic substrate of high mechanical resiliency, wherein the substrate comprises, within the volume thereof, inclusions of polymerized hydrophilic substances, grafted on the hydrophobic substrate and cross-linked, in which water-soluble histidine salt has been stored and which will perfuse through the hydrophobic substrate when the latter is placed in an aqueous medium. Materials suitable for the hydrophobic substrate are polymerized thermoplastic products such as, e.g., vinyl acetate, polyethylene or a co-polymer of vinyl acetate and polyethylene, or, more generally, an ethylene co-polymer, a polyether, a polyurethane or a polyacrylonitrile. Materials suitable for the hydrophilic substances include ethylene-glycol acrylate, ethylene-glycol methacrylate, acrylamide, methacrylamide, acrylamide methylol, acrylamide diacetone or an unsaturated acidic product such as malic acid, acrylic acid, methacrylic acid, fumaric acid, itaconic acid or propylene glycol acrylate or methacrylate. Also polypropylene, polyamides, polyesters such as ethylenglycol, polyterephtalate, polyvinyl chloride, polyformaldehyde chloride, polycarbonates and olytetrafluoroethylene ("Teflon") may be used. In addition to storing therapeutic amounts of histidine salt in the hydrophilic inclusions, contraceptive agents such as copper-, zinc-, cobalt-, lead- and cadmium-salts, synthetic progestational sexual steroids (such as derivatives of testosterone, the derivatives of nortestosterone, norethisterone, norethisterone acetate, norethynodrel, ethynodiol diacetate, norgestrienone, norgestrel, chlormadynone acetate, medroxyprogesterone acetate, megestrol acetate, anagestrone acetate and prostaglandine) and ovulation inhibiting oestrogens (such as ethynol oestradiol and mestranol).

For an intrauterine device that is at least partially bio-erodible, the materials must be non-toxic and non-irritating to the endometrium of the uterus, and the bioerosion end products of which must also be non-toxic and easily eliminated from the body. Exemplary bioerodible materials include both natural and synthetic materials such as (a) structural proteins and hydrocolloids of animal origin; (b) polysaccharides and other hydrocolloids of plant origin; and (c) synthetic polymers. Some of these matrix materials are suitable as in their native form but others, particularly hydrocolloids, require insolubilization either by chemical modification, or physical modification, such as orientation, radiation cross-linking, etc. Exemplary of the first category are: native and modified collagens, muscle proteins, elastin, keratin, resilin, fibrin, etc. Exemplary of polysaccharides and plant hydrocolloids are: a ligin, pectin, carrageenin, chitin, heparin, chondroitin sulfate, Agar-agar, Guar, locust bean gum, gum arabic, gum Karaya, tragacanth, gum Ghatti, starch, oxystarch, starch phosphate, carboxymethyl starch, sulfaethyl starch, aminoethyl starch, amido ethyl starch, starch esters such as starch maleate, succinate, benzoate and acetate, and mixtures of starch and gelatin; cellulose and its derivatives such as modified cellulosics, such as partially hydroxyethylated cotton obtained by the treatment of cotton with ethylene oxide or partially carboxymethylated cotton obtained by the treatment of cotton with caustic and choroacetic acid. Exemplary of synthetic polymers are: poly(vinyl alcohol), poly(ethylene oxide), poly(acrylamide), poly(vinyl pyrrolidone), poly(ethyleneimine), poly(vinyl imidazole), poly(phosphate), synthetic polypeptides, polyvinyl alkyl ether, polyacryl-and polymethacrylamides, and copolymers of acrylamide and methacrylamide with up to 40% by weight of N-methylene bisacrylamide or N,N-dimethylol urea; polyalkyl aldehydes, water soluble hydrophilic polymers of uncross-linked hydroxyalkyl acrylates and methacrylates, polyalkylene carbonates, and the like. The list is illustrative. Any bioerodible material which is compatible with histidine and non-toxic and which has the desired erosion and release rates can be used. Typically cross-linking agents(e.g., aldehydes, such as acetaldehyde, formaldehyde, acrolein, crotonaldehyde, glutaraldehyde, glyoxal, dimethylol urea, trimethylol melamine; tetra (methoxymethyl) urea, melamine, epichlorohydrin, and hexamethylene tetramine) and plasticizers (e.g., acetyl tri-n-butyl citrate, epoxidized soy bean oil, glycerol monoacetate, polyethylene glycol, propylene glycol dilaurate, decanol, dodecanol, 2-ethyl hexanol, 2,2-butoxyethoxyethanol and the like) are added to impart the desired rate of bioerosion and flexibility, respectively, to the IUD.

For intranasal administration of histidine, the choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives (e.g., antimicrobials), surfactants (e.g., non-ionics such as polysorbates) gelling agents, buffering and other stabilizing agents (e.g., antioxidants and metal chelating agents) and solubilizing agents (e.g., solubility enhancers) may also be present. Preferably, the nasal dosage form should be isotonic with nasal secretions. Although histidine can be formulated in water, more preferably it will be formulated in a solution buffered to a pH of between about 3.0 and 8.0, and most preferably pH 5.0–5.4 using e.g., a buffer system such as an acetate buffer, a phosphate buffer, a citrate buffer, and a succinate buffer.

For oral administration, histidine is formulated with a pharmaceutically acceptable solid or liquid carrier. Solid form preparations include powders, tablets, pills, capsules, cachets, and dispersible granules. A solid carrier can be one or more substances which may also act as diluents, flavoring agents, solubilizers, lubricants, suspending agents, binders, preservatives, tablet disintegrating agents, or encapsulating materials. These may also include one or more excipients that is a selectively porous or slowly-dissolving layer-forming material or nonlayer-forming material (e.g., polymeric materials) in order to render the oral dosage form sustained- or controlled-release.

In powders, the carrier is a finely divided solid which is in a mixture with the finely divided active component. In tablets, the active component is mixed with the carrier having the necessary binding properties in suitable proportions and compacted in the shape and size desired.

The powders, capsules and tablets preferably contain from five or ten to about seventy percent of the active compound. Suitable carriers are magnesium carbonate, magnesium stearate, talc, sugar, lactose, pectin, dextrin, starch gelatin, tragacanth, methylcellulose, sodium carboxymethylcellulose, microcrystalline cellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

Another type of solid carrier useful in the practice of the invention is a foodstuff. Solid foodstuffs suitable for admixture with a therapeutic dosage or unit dosage of histidine are, for example, a cereal product, chewing gum, or a candy lozenge. For veterinary applications, histidine may be admixed directly into a grain ration of incorporated into a salt block. Likewise, histidine may be formulated with a liquid foodstuff, for example, milk, juices, liquid vitamin supplements, and oral rehydration solutions (e.g., in those cases where dysmenorrhea causes diarrhea).

Liquid form preparations include solutions, suspensions, emulsions, for example, of water aqueous solution, or other liquids, half-liquid bases, or optionally in pharmaceutically acceptable solvents (e.g., DMSO-propylene glycol solutions).

Also included are solid form preparations which are intended to be converted, shortly before use, to liquid for preparation for oral or rectal administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, lotions, ointments and powders in vials or ampoules. Also, the unit dosage form can be a capsule, tablet, cachet, or lozenge itself, or it can be the appropriate number of any of these in packaged form.

It is also within the scope of the invention to administer histidine in a time-release formulation such as a bolus for veterinary therapies. A wide variety of methods are now available in the art for preparing time-release or long-acting compositions. Any of these time-release or long-acting formulations are suitable in the practice of the present invention as long as it does not adversely affect the effectiveness of histidine in the treatment or prevention of extracellular fluid secretions and fluid/electrolyte losses. Advantages of time-release formulations include a lower concentration of peak serum absorption which substantially reduces any possible adverse side effects and/or toxicity of the active administered. In addition, a reduced frequency of administration results, which substantially improves patient compliance. A frequency of administration of every 12 to 24 hours would be preferred. In addition, a more constant concentration of histidine would result, and consequently, a more consistent relief or prophylaxis of symptoms.

EXAMPLES

The following examples are provided to illustrate, not limit, the scope of the invention.

CAPSULE FORM

A) A capsule (22 mm length, 8 mm dia) was filled with a mixture that was prepared by combining 20 g of L-histidine free base with 60 g of lactose. One capsule contained 20 mg of the active substance.
B) Similarly, a capsule was prepared with a 100 mg dose of L-histidine free base by thoroughly admixing 100 mg dose of L-histidine with 100 g of lactose and filling a capsule of appropriate dimension.

Histidine-containing Soft Gelatin Capsules can be Prepared as Follows

C) A mixture was formed by combining 500 mg of L-histidine free base with 10 mg of lecithin, 20 mg of beeswax and 420 mg of soybean oil. The mixture was encapsulated into a 16 oblong soft gelatin capsule. One capsule contains 500 mg of the active substance.
D) Similarly, a 250 mg dose of L-histidine was prepared by thoroughly admixing 250 mg of L-histidine free base with 5 mg of lecithin, 10 mg of beeswax, and 210 mg of soybean oil, and then encapsulated into a soft gelatin capsule of appropriate dimension.

TABLET FORM

A) 10 g of histidine were mixed with 60 g of lactose and 138 g of starch whereupon the mixture was wetted by a necessary amount of starch hydrogel. Two grams of magnesium stearate were added to the mixture after it was granulated and homogenized.

The mixture was then pressed to tablets. Each tablet was about 250 mg weight and 5 mm diameter and contained a 10 mg dose of the active substance.
B) Similarly, 500 mg tablets were prepared in which an amount of histidine corresponding to the 500 mg dose was added to proportionate amounts of lactose, starch hydrogel, and magnesium stearate, followed by granulating, homogenization, and pressing into tablets.
C) A tablet containing 250 mg of amoxicillin trihydrate and 200 mg of L-histidine was formulated with citric acid, corn starch, FD & C Red No. 40, flavoring, mannitol, magnesium stearate, saccharin sodium, silica gel and sucrose, in quantities routinely determined in the formualtion art.

SUPPOSITORY FORM 7.5 g of L-histidine was dispersed into purified water and 3 g of a fatty acid triglyceride was added to the dispersion. After stirring to homogenize base was added in an amount to make the mixture pH 7.0, followed by the addition of purified water in an amount appropriate to make 100 g of a transparent gel with stirring. The gel was filled in 2.5 cc disposable syringes to obtain 50 pieces of syringed L-histidine injection preparation, each weighing 2 g and containing 150 mg of L-histidine.

I.V. SOLUTION

A) A typical i.v. solution for practice of the invention can be prepared by dissolving a specified number of moles of histidine to obtain the desired dose in sterilized water while stirring the solution to homogeneity. Acetic acid is added to the resulting aqueous solution of histidine to adjust the same to a pH of 7.0. The resulting aqueous solution is subjected to milipore filtration and charged under nitrogen gas into a vessel for an infusion solution. The product infusion solution was obtained by autoclaving under the usual conditions.
B) A combination therapy ready-for-use i.v. solution containing 0.2% ciprofloxacin and 10% L-histidine in a 5% dextrose solution, solubilized with lactic acid, and pH adjusted with HCl.

| SOLUTION FOR NASAL ADMINISTRATION | |
|---|---|
| L-histidine | 0.02–2 g |
| Sodium Acetate | 0.300 g |
| Methylparaben | 0.100 g |
| Propylparaben | 0.020 g |
| Sodium chloride | As needed for tonicity |
| Hydrochloric Acid or Sodium Hydroxide | To adjust pH |
| Purified Water | To 100 mL |

OINTMENT FOR TRANSDERMAL ADMINISTRATION

The following components are thoroughly admixed:
A) L-histidine 150 mg polyethylene glycol (avg. Mol. Wt. 1500) 120 mg polyethylene glycol (avg. Mol. Wt. 400) 240 mg

| A) L-histidine | 150 mg |
|---|---|
| polyethylene glycol (avg. Mol. Wt. 1500) | 120 mg |
| polyethylene glycol (avg. Mol. Wt. 400) | 240 mg |
| B) L-histidine | 50 mg |
| vaselin | 710 mg |
| paraffin liquid | 240 mg |

TRANSDERMAL PATCH FORMULATION

| histidine HCl salt | 1–20% |
|---|---|
| vaselin | 20% |
| paraffin | 5% |
| polysiloxane adhesive | 55% |

Histidine hydrochloride salt is added under thorough mixing to a mixture of vaselin and paraffin (mixture I). The silastic elastomer is weighed directly to a tared mould to which mixture I is added and mixed thoroughly before adding a curing agent. The formulation is allowed to cure for 48 hours at room temperature and protected from light.

TAMPON CONTAINING HISTIDINE

A tampon is made by providing a first sheet of absorbent material to form the corpus of the tampon, and overlaying the first sheet with a second overwrap sheet of non-woven material which is permeable by body fluids. L-Histidine in a suitable carrier is deposited at a concentration of 10 mg/cm$^2$ between the overwrap and corpus sheets. In another form of the invention, the overwrap sheet is impregnated with the L-histidine at the same concentration outlined above. The sheets are superimposed and then rolled and formed into the desired shape of the tampon with the overwrap sheet on the outside thereof so that the medicament is disposed nearest the outside of the tampon.

Other methods of impregnating tampons or manufacturing tampons with medicaments such as histidine are those found in U.S. Pat. Nos. 4,186,742; 4,340,055; 4,582,717; 5,201,326 and 5,417,224 the entire contents of which are incorporated by reference herein.

INTRA-UTERINE DEVICE CONTAINING L-HISTIDINE

A bioerodible intrauterine device containing L-Histidine is prepared in the following manner:

A. Preparation of Zinc Alginate 1. seven grams of sodium alginate (Keltone, Kelco Co., KT-9529-21) is dissolved in 350 ml of distilled water by means of efficient stirring, to yield a slightly viscous solution.

2. In a separate preparation, 10 grams of zinc chloride is dissolved in 600 ml of distilled water and the pH is adjusted to 3 by drop-wise addition of concentrated hydrochloric acid.

3. To the zinc chloride is added in small proportions the sodium alginate solution under moderate agitation. The mixture is vigorously stirred for 10–15 minutes, and allowed to stand overnight.

4. The precipitate is washed continuously with distilled water to a negative silver chloride test (or to the same conductivity reading as distilled water). The aqueous suspension of the sodium chloride-free zinc alginate is isolated by lyophilization and vacuum-dried at 40° C. overnight.

B. Preparation of L-Histidine Uterine Insert

1. The mixture containing 4.5 grams of micronized L-Histidine in 3.5 grams of glycerine is homogenized by means of a suitable colloid mill or by simple grinding of the mixture with mortar and pestle.

2. The resulting white paste is slowly poured into 100 ml of 1.2% ammonium hydroxide solution under vigorous agitation. To this suspension is added 10 grams of zinc alginate previously prepared, and the vigorous agitation is continued until the complete dissolution of the zinc alginate results; if marked thickening occurs, more ammonia solution can be added.

3. The viscous dispersion of (5) is drawn on a glass plate with a wet thickness of ca. 10 mils. The cast plate is placed in a circulating stream of warm, moisturized air at 40° C., and allowed to dry thoroughly.

4. The resulting film is removed from the plate by stripping, and is cut into desired shape and size. For example, a 3 mm×10 mm device of 3 mil thickness contains about 135 mg of L-histidine. When inserted in a monkey's uterus, the resulting device releases the L-Histidine over a two-day period.

Other IUD's can be manufactured containing L-Histidine using the methods outlined in U.S. Pat. Nos. 3,934,580; 3,993,057 and 4,016,270.

BIOADHESIVE FILM COMPOSITION 6.72 Grams of p-HEMA as medicinally inert matrix were dissolved in 26 milliliters of dimethyl formamide (DMF), and 3 grams of L-Histidine as treating agent were admixed with the resulting soltuion. The treating agent-matrix solution was poured into a glass petri dish having an area of 63.585 cm2 and dried to form a film. The film so prepared had a thickness of 2000±200 microns.

830 Milligrams of polycarbophil (polyacrylic acid crosslinked with divinyl glycol—A. H. Robins Co. of Richmond, Va.) sieved to a 30/40 mesh size were swollen in 12 milliliters of a solution that contained 6 parts of water and 2 parts of DMF, by volume. The above-prepared film was wetted by a fine spray of DMF. About one minute thereafter, the swollen bioahesive was evenly spread over the wet surface of the film using a spatula. The film composition of this invention so prepared was then dried at room temperature.

After drying, a second, similar amount of bioadhesive was spread over the second surface of the film composition to form another composition of this invention. The second composition was dried again at room temperature and then cut into rectangularly shaped pieces having dimensions of about 2×3 millimeters. The above pieces are use for vaginal delivery of L-histidine.

The invention now being fully described, it will be apparent to one of ordinary skill in the art that many changes and modifications can be made thereto without departing from the spirit or scope of the invention as set forth herein. It is therefore to be understood that within the scope of the appended claims, the invention may be practiced otherwise than as specifically described herein.

What We claim is:

1. A method for preventing the onset of dysmenorrhea or treating the sequelae thereof in a human female, said method comprising administering to said human female at a time prior to menses or at commencement thereof, or both, an amount of D-histidine, L-histidine, a therapeutically acceptable salt of histidine which can be reduced to D- or L-histidine, or mixtures thereof, that is effective to prevent onset of dysmenorrhea or to treat the sequelae thereof, in conjunction with at least one pharmacologically acceptable carrier.

2. The method according to claim 1 wherein said step of administering histidine comprises oral, rectal, vaginal, intraintestinal, intramuscular, intraperitoneal, intranasal, intravenous, cervical implant, transmucosal, transdermal administration, or combinations thereof.

3. The method according to claim 2 wherein said step of administering histidine comprises vaginal, cervical or uterine implant, transmucosal, or oral administration, or combinations thereof.

4. The method according to 3 wherein said step of administering histidine comprises vaginally administering a prophylactically or therapeutically effective amount of said histidine in conjunction with a bioadhesive crosslinked carboxylic acid polymer as a sustained release carrier.

5. The method according to claim 1 wherein said prophylactically or therapeutically efective amount of histidine is an amount of from about 500 mg to 30 g daily.

6. The method according to claim 5 wherein said prophylactically or therapeutically effective amount of histidine is administered as early as one day prior to commencement of ovulation in a menstrual cycle.

7. The method according to claim 5 wherein said prophylactically or therapeutically effective amount of histidine is administered as early as one day prior to a first day of menstruation and continually administered so long as sequelae of dysmenorrhea persist.

8. The method according to claim 3 wherein said prophylactically or therapeutically effective amount of histidine is administered intravaginally in a form comprising a medicated tampon, a cream, a gel, a foam, or a suppository, or as a histidine-releasing intrauterine device.

9. The method according to claim 3 wherein said prophylactically or therapeutically effective amount of histidine is administered orally, optionally in a controlled-release dosage form.

10. The method according to claim 8 wherein said amount of histidine is administered from a sustained-release coat on or reservoir within said histidine-releasing intrauterine device.

11. The method according to claim 10 wherein said amount of histidine is administered from an intrauterine device having crosslinked carboxylic acid polymer coat thereon.

12. The method according to claim 1 wherein said dysmenorrhea is a primary or a secondary dysmenorrhea.

13. The method according to claim 12 wherein said secondary dysmenorrhea treated is a sequela of an underlying pathologic condition selected from the group consisting of endometriosis, pelvic inflammation, pelvic infection, adenomyosis, uterine myoma, uterine polyps, uterine adhesions, congenital malformations of the Mullerian system, cervical stenosis, ovarian cysts, pelvic congestion syndrome, polycystic ovary syndrome, and Allen-Master's syndrome.

14. The method according to claim 12 wherein said dysmennorrhea is a secondary dysmenorrhea arising from an intrauterine device present in said human female.

15. The method according to claim I further comprising co-administering a second compound which is a therapeutic agent for preventing or treating dysmenorrhea other than histidine, and wherein said second compound is efficaciously co-administered in an amount which is less than an pharmacologically recommended dose for said second compound when administered alone.

16. The method according to claim 15 wherein said second compound comprises a prostaglandin synthetase inhibitor.

17. The method according to claim 16 wherein said prostaglandin synthetase inhibitor comprises a nonsteroidal antiinflammatory agent.

18. A method for treating pelvec pain from endometriosis in a human female, comprising administering to said human female an amount of D-histidine, L-histidine, a therapeutically acceptable salt of histidine which can be reduced to D- or L-histidine, or mixtures thereof, that is effective to alleviate said pelvic pain, in conjunction with at least one pharmacologically acceptable carrier.

19. The method according to claim 18 wherein said prophylactically or therapeutically effective amount of histidine is an amount of from about 500 mg to 30 g daily.

20. The method according to claim 18 wherein said step of administering histidine comprises oral, rectal, vaginal, intraintestinal, intramuscular, intraperitoneal, intranasal, intravenous, cervical implant, transmucosal, transdermal administration, or combinations thereof.

21. The method according to claim 20 wherein said step of administering histidine comprises vaginal, cervical or uterine implant, transmucosal, or oral administration, or combinations thereof.

22. The method according to claim 18 wherein said step of administering histidine comprises vaginally administering a therapeutically effective amount of said histidine in conjunction with a bioadhesive crosslinked carboxylic acid polymer as a sustained release carrier.

23. The method according to claim 21 wherein said prophylactically or therapeutically effective amount of histidine is administered intravaginally in a form comprising a medicated tampon, a cream, a gel, a foam, or a suppository, or as a histidine-releasing intrauterine device.

24. The method according to claim 21 wherein said prophylactically or therapeutically effective amount of histidine is administered orally, optionally in a controlled-release dosage form.

25. The method according to claim 18 further comprising co-administering a second compound which is a therapeutic agent for treating endometriosis and sequelae thereof other than histidine, and wherein said second compound is efficaciously co-administered in an amount which is less than an pharmacologically recommended dose for said second compound when administered alone.

26. A method for preventing onset of or controlling a pre-term labor in a pregnant woman, comprising administering to said pregnant woman an amount of D-histidine, L-histidine, a therapeutically acceptable salt of histidine which can be reduced to D- or L-histidine, or mixtures thereof, that is effective to prevent, or control by extending to substantially full-term, a pre-term labor, in conjunction with at least one pharmacologically acceptable carrier.

27. The method according to claim 26 wherein said amount of histidine is an amount of from about 500 mg to 30 g daily.

28. The method according to claim 26 wherein said amount of histidine is administered to a pregnant woman experiencing pre-term labor for a period of time sufficient to extend a potential pre-term delivery to substantially a full-term delivery.

29. The method according to claim 26 wherein said step of administering histidine comprises oral, rectal, vaginal, intraintestinal, intramuscular, intraperitoneal, intranasal, intravenous, cervical or uterine implant, transmucosal, transdermal administration, or combinations thereof.

30. The method according to claim 29 wherein said step of administering histidine comprises vaginal, cervical or uterine implant, transmucosal, or oral administration, or combinations thereof.

31. The method according to 26 wherein said step of administering histidine comprises vaginally administering a therapeutically effective amount of said histidine in conjunction with a bioadhesive crosslinked carboxylic acid polymer as a sustained release carrier.

32. The method according to claim 30 wherein said prophylactically or therapeutically effective amount of histidine is administered intravaginally in a form comprising a medicated tampon, a cream, a gel, a foam, or a suppository, or as a histidine-releasing intrauterine device.

33. The method according to claim 30 wherein said prophylactically or therapeutically effective amount of histidine is administered orally, optionally in a controlled-release dosage form.

34. The method according to 26 wherein said step of administering histidine comprises vaginally administering a therapeutically effective amount of said histidine in conjunction with a bioadhesive crosslinked carboxylic acid polymer as a sustained release carrier.

35. The method according to claim 26 further comprising co-administering a second compound which is a pre-term labor inhibiting therapeutic agent other than histidine, and wherein said second compound is efficaciously co-administered in an amount which is less than an pharmacologically recommended dose for said second compound when administered alone.

36. A method for preventing or treating pre-menstrual and menstrual cramping in a woman, comprising administering either before onset of menses or at commencement thereof, or both, a prophylactically or therapeutically effective amount of D-histidine, L-histidine, a therapeutically acceptable salt of histidine which can be reduced to D- or L-histidine, or mixtures thereof, in conjunction with at least one pharmacologically acceptable carrier.

37. The method according to claim 36 wherein said step of administering histidine comprises oral, rectal, vaginal, intraintestinal, intramuscular, intraperitoneal, intranasal, intravenous, implant, transdermal administration, or combinations thereof.

38. The method according to claim 37 wherein said step of administering histidine comprises vaginal, uterine implant, suppository, oral administration, or combinations thereof.

39. The method according to 38 wherein said step of administering histidine comprises vaginally administering a prophylactically or therapeutically effective amount of said histidine in conjunction with a bioadhesive crosslinked carboxylic acid polymer as a sustained release carrier.

40. The method according to claim 36 wherein said prophylactically or therapeutically effective amount of histidine is an amount of from about 500 mg to 30 g daily.

41. The method according to claim 40 wherein said prophylactically or therapeutically effective amount of histidine is administered as early as one day prior to commencement of ovulation in a menstrual cycle.

42. The method according to claim 40 wherein said prophylactically or therapeutically effective amount of histidine is administered a) either as early as one day prior to a first day of menstruation or on first occurrence of menstrual cramps and b) continually administered for as many days of menses that menstrual cramps persist.

43. The method according to claim 36 wherein said prophylactically or therapeutically effective amount of histidine is administered intravaginally before or during menstruation in a form comprising a medicated tampon, a cream, a gel, a foam, a suppository, or a histidine-releasing intrauterine device.

44. The method according to 36 wherein said step of administering histidine comprises vaginally administering a therapeutically effective amount of said histidine in conjunction with a bioadhesive crosslinked carboxylic acid polymer as a sustained release carrier prior to and during menstruation.

45. The method according to claim 36 wherein said prophylactically or therapeutically effective amount of histidine is administered orally in a controlled-release dosage form.

46. The method according to claim 43 wherein said amount of histidine is administered from a sustained-release coat on or reservoir within said histidine-releasing intrauterine device.

47. The method according to claim 46 wherein said amount of histidine is administered from an intrauterine device having crosslinked carboxylic acid polymer coat thereon.

48. The method according to claim 36 further comprising co-administering a second compound which is a menstrual cramp-alleviating therapeutic agent other than histidine, and wherein said second compound is efficaciously co-administered in an amount which is less than an pharmacologically recommended dose for said second compound when administered alone.

49. A method for preventing or controlling a pre-term labor in an insulin-resistant pregnant woman, comprising administering to said insulin-resistant pregnant woman A) an amount of D-histidine, L-histidine, a therapeutically acceptable salt of histidine which can be reduced to D- or L-histidine, or mixtures thereof, that is effective to prevent, or control by extending to substantially full-term, said pre-term labor and B) an effective amount of D-chiroinositol, in conjunction with at least one pharmacologically acceptable carrier.

50. The method according to claim 49 wherein said amount of histidine is from about 500 mg to 30 g daily.

51. A composition of matter for preventing or treating dysmenorrhea and sequelae thereof in a human female, comprising one of an intravaginal device or an intrauterine device containing a releasable prophylactically or therapeutically effective amount of D-histidine, L-histidine, a therapeutically acceptable salt of histidine which can be reduced to D- or L-histidine, or mixtures thereof.

52. The composition according to claim 51 which is a tampon having incorporated therein or on a n exterior surface thereof, or both, a releasable prophylactically or therapeutically effective amount of D-histidine, L-histidine, a therapeutically acceptable salt of histidine which can be reduced to D- or L-histidine, or mixtures thereof.

53. The composition according to claim 51 which is an intrauterine device having incorporated therein or thereon, or both, a releasable prophylactically or therapeutically effective amount of D-histidine, L-histidine, a therapeutically acceptable salt of histidine which can be reduced to D- or L-histidine, or mixtures thereof.

54. A composition for treating endometriosis and sequelae thereof comprising A) a therapeutically effective amount of D-histidine, L-histidine, a therapeutically acceptable salt of histidine which can be reduced to D- or L-histidine, or mixtures thereof, B) an effective amount of a hormone therapeutic selected from the group consisting of danazol, a gonadotropin releasing hormone analogue, and an oral contraceptive, and pharmacologically acceptable carrier therefor.

55. A composition for treating a woman afflicted with polycystic ovary syndrome, comprising A) a therapeutically effective amount of D-histidine, L-histidine, a herapeutically acceptable salt of histidine which can be reduced to D- or L-histidine, or mixtures thereof, B) an ovulation-restoring effective amount of D-chiroinositol, and pharmacologically acceptable carrier therefor.

56. A composition for preventing onset of or for treating dysmenorrhea in a human female, comprising A) an effective amount of D-histidine, L-histidine, a therapeutically acceptable salt of histidine which can be reduced to D- or L-histidine, or mixtures thereof, B) an amount of a prostaglandin synthetase inhibitor which is less than a pharmacologically recommended dose for said prostaglandin synthetase inhibitor when administered alone and which amount is efficacious when co-administered with said histidine, and pharmacologically acceptable carrier therefor.

57. The composition according to claim 56 wherein said prostaglandin synthetase inhibitor comprises at least one nonsteroidal antiinflammatory agent.

58. A composition for suppressing or managing pre-term labor in a pregnant female mammal comprising A) a premature labor inhibiting effective amount of D-histidine, L-histidine, a therapeutically acceptable salt of histidine which can be reduced to D- or L-histidine, or mixtures thereof, B) a second active agent other than histidine and useful for controlling premature labor, present in an amount which is less than a pharmacologically recommended dose for said second active compound when administered alone, and which amount of said second active agent is efficacious when co-administered with said histidine, and a pharmacologically acceptable carrier therefor.

59. The composition according to claim 58 wherein said pharmacologically active compound B) comprises a tocolytic oxytocin receptor antagonist, an aromatase inhibitor, an activin antagonist, a 3-hetero-substituted- N-benzyl-indole leukotriene biosynthesis inhibitor, or a S-nitrosothiol compound.

60. A composition for vaginal delivery of a prophylactic or therapeutic amount of D-histidine, L-histidine, a therapeutically acceptable salt of histidine which can be reduced to D- or L-histidine, or mixtures thereof, said composition comprising a prophylactically or therapeutically effective amount of said histidine and a bioadhesive crosslinked carboxylic acid polymer as a carrier.

61. A treatment method for polycystic ovary syndrome and for dysmenorrhea as a sequela of said treatment in a woman, comprising co-administering to said woman an ovulation-restoring effective amount of D-chiroinositol, a therapeutically effective amount of D-histidine, L-histidine, a therapeutically acceptable salt of histidine which can be reduced to D- or L-histidine, or mixtures thereof, and at least one pharmacologically acceptable carrier.

* * * * *